(12) United States Patent
Winton et al.

(10) Patent No.: US 11,620,100 B2
(45) Date of Patent: Apr. 4, 2023

(54) SYSTEMS AND METHODS FOR ADJUSTING ACTIVITY CONTROL PARAMETERS

(71) Applicant: Harman International Industries, Incorporated, Stamford, CT (US)

(72) Inventors: Riley Winton, Opelika, AL (US); Christopher Michael Trestain, Livonia, MI (US); Chris Ludwig, Bloomfield Hills, MI (US); Maxwell Willis, Royal Oak, MI (US)

(73) Assignee: Harman International Industries, Incorporated, Stamford, CT (US)

( * ) Notice: Subject to any disclaimer, the term of this patent is extended or adjusted under 35 U.S.C. 154(b) by 0 days.

(21) Appl. No.: 16/950,670

(22) Filed: Nov. 17, 2020

(65) Prior Publication Data
US 2021/0200506 A1     Jul. 1, 2021

Related U.S. Application Data

(60) Provisional application No. 62/954,195, filed on Dec. 27, 2019.

(51) Int. Cl.
| | | |
|---|---|---|
| *G06F 3/16* | (2006.01) | |
| *H04R 1/22* | (2006.01) | |
| *H04R 3/00* | (2006.01) | |

(52) U.S. Cl.
CPC ............. *G06F 3/165* (2013.01); *H04R 1/22* (2013.01); *H04R 3/00* (2013.01); *H04R 2430/01* (2013.01); *H04R 2499/13* (2013.01)

(58) Field of Classification Search
CPC .. G06F 3/165; H04R 1/22; H04R 3/00; H04R 2430/01; H04R 2499/13
See application file for complete search history.

(56) References Cited

U.S. PATENT DOCUMENTS

| | | | |
|---|---|---|---|
| 8,030,871 B1 * | 10/2011 | Young | A63H 19/24 |
| | | | 446/7 |
| 2009/0292993 A1 * | 11/2009 | Ulrich | G06F 3/0481 |
| | | | 715/727 |
| 2015/0025662 A1 * | 1/2015 | Di Censo | G06F 3/011 |
| | | | 700/94 |
| 2021/0303258 A1 * | 9/2021 | Tanaka | G06F 3/167 |

OTHER PUBLICATIONS

"Rainforest—Interactive Tropical Forest Soundscape," My Noise Website, Available Online at https://mynoise.net/NoiseMachines/rainforestNoiseGenerator.php, Available as Early as Jan. 29, 2016, 2 pages.
Winton, R. et al., "Systems and Methods for Providing Nature Sounds," U.S. Appl. No. 17/112,684, filed Dec. 4, 2020, 84 pages.
(Continued)

*Primary Examiner* — Joseph Saunders, Jr.
(74) *Attorney, Agent, or Firm* — McCoy Russell LLP

(57) ABSTRACT

Systems and methods for generating sounds in a vehicle or other location are presented. In one example, a single user input may be a basis for adjusting a sound level and a frequency of occurrence of a sound that is stored in controller memory and that is output via one or more speakers.

19 Claims, 9 Drawing Sheets

(56) References Cited

OTHER PUBLICATIONS

Tan, P., "Mercedes-Benz MyCOMAND features 'Cover Flow'," PAULTAN Website, Available Online at https://paultan.org/2008/12/07/mercedes-benzs-new-mycomand-features-cover-flow/, Dec. 7, 2008, 1 page.

Hastrup, S., "Recomposing Soundscapes: A Workbook documenting the creative process of making a Mobile Reactive Music prototype for a master's thesis," Workbook Sebsongs Website, Available Online at http://workbook.sebsongs.com/tag/mobmuplat/, Available as Early as Apr. 26, 2017, 7 pages.

Akai, Y. et al., "Interactive soundscape system utilising the automobile," Proceedings of the 2018 NICOGRAPH International, Jun. 28, 2018, Tainan, Taiwan, 6 pages.

European Patent Office, Partial European Search Report Issued in Application No. 20213984.6, dated May 18, 2021, Germany, 15 pages.

\* cited by examiner

SYSTEMS AND METHODS FOR ADJUSTING ACTIVITY CONTROL PARAMETERS

CROSS REFERENCE TO RELATED APPLICATIONS

The present application claims priority to U.S. Provisional Application No. 62/954,195, entitled "SYSTEMS AND METHODS FOR ADJUSTING ACTIVITY CONTROL PARAMETERS", and filed on Dec. 27, 2019. The entire contents of the above-listed application are hereby incorporated by reference for all purposes.

BACKGROUND

The disclosure relates to sounds, which may be output in a vehicle.

SUMMARY

Some infotainment systems include prerecorded sounds from actual natural settings or artificially generated sounds that may be played back in the form of audio sounds to human users. For example, infotainment system users may hear only one sound from a group of sounds. The group of sounds may include the sound of rain falling, waterfalls, ocean waves, or thunder, for example. The user may select the sound to be played back and the sound may be played back over speakers in a vehicle so that the human users may experience a sensation, such as being relaxed or calm. Hearing the sounds may also reduce stress and anxiety for human users. The infotainment system may also display scenes that correspond to the sounds being played so as to further enhance the user experience. Although, the sounds and scenes may succeed in setting a mood or environment for users, the sounds and scenes may be static and inflexible. In particular, the volume or sound power level may be the only aspect of prerecorded or artificially generated sounds that may be adjusted. Consequently, users may show less interest in the prerecorded sounds once they become accustomed to hearing the sounds. In addition, each prerecorded or artificially generated sound may be useful for only setting conditions to bring about only one user mood or psychological state of mind.

The inventors have recognized the previously mentioned issues and have developed systems and methods to at least partially address the above issues. In particular, the inventors have developed a method for generating sounds in a vehicle, comprising: generating sounds according to a state of a user control that includes an operating range that is subdivided into a plurality of group regions, each of the plurality of group regions associated with one or more elements unique to a group region within the plurality of group regions.

By generating sounds according to a position of a user control that includes an operating range that is subdivided into a plurality of group regions, it may be possible to combine two or more sounds to increase the diversity of sound generated via an infotainment center. Further, a base sound may be augmented with additional sounds, modified in frequency of repetition, and adjusted in sound output power level so as to provide a range of mood changing or enhancing sounds. Consequently, functionality of an infotainment system or audio system may be improved while ease of system control may be provided via a position of a sole user control.

The present description may provide several advantages. Specifically, the approach may increase diversity of mood changing sounds that may be available to system users. In addition, the approach may provide increased functionality via a simple single user input. Further, the approach allows a user to change an intensity level of an experience via the same single input.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

The present disclosure relates to generating sounds according to user input. The generating of sound includes generating sounds in a first group of sounds according to a position or state of a user input and adding additional sounds to the first group of sounds as a position or state of the user input is changed. Further, the user input may control a volume or sound output power level (e.g., decibels (dB)) and a frequency at which activated sounds are repeated when the sounds are being generated.

Figure 1:
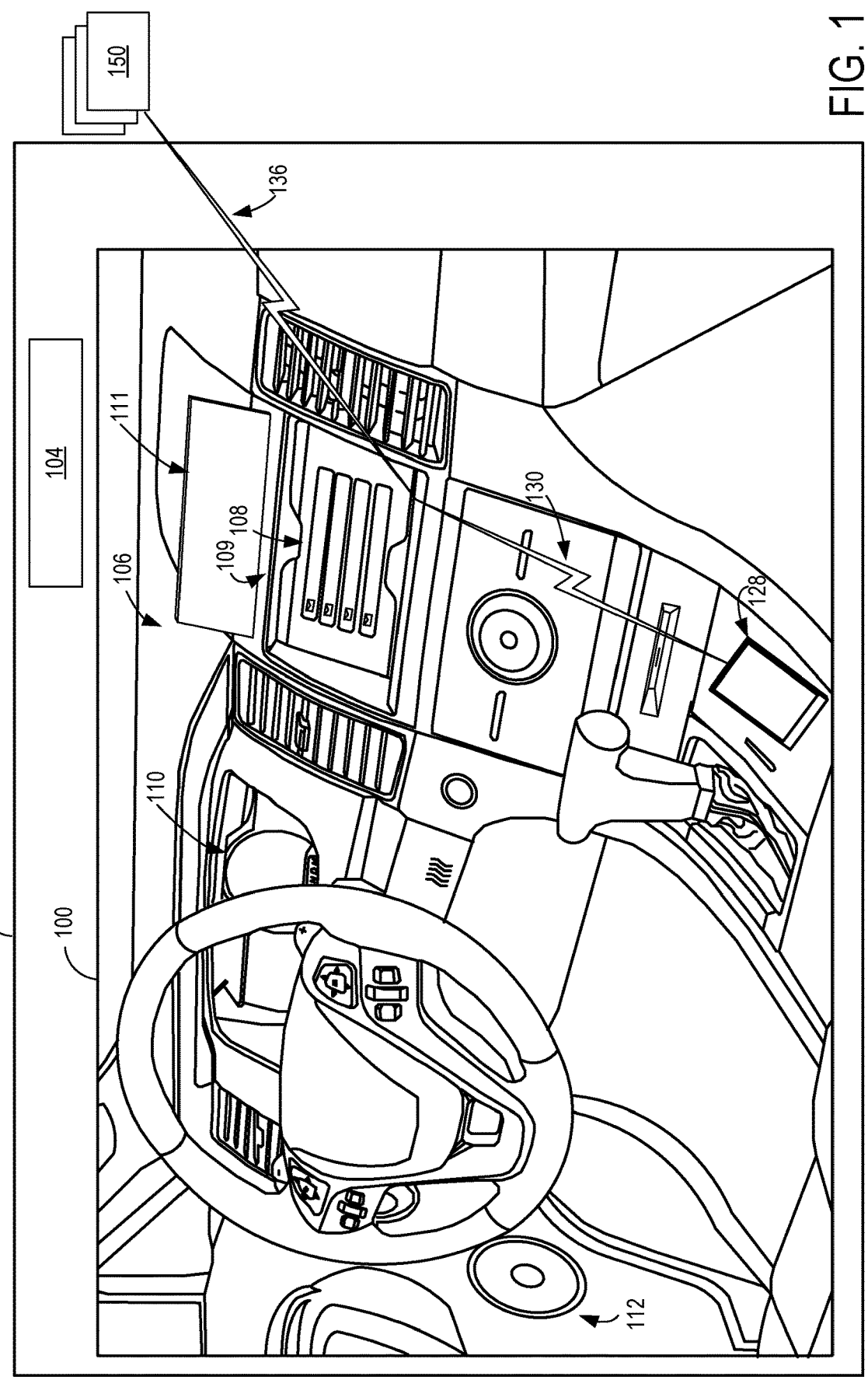
FIG. 1 shows an example partial view of a vehicle cabin in accordance with one or more embodiments of the present disclosure.
Figure 2:
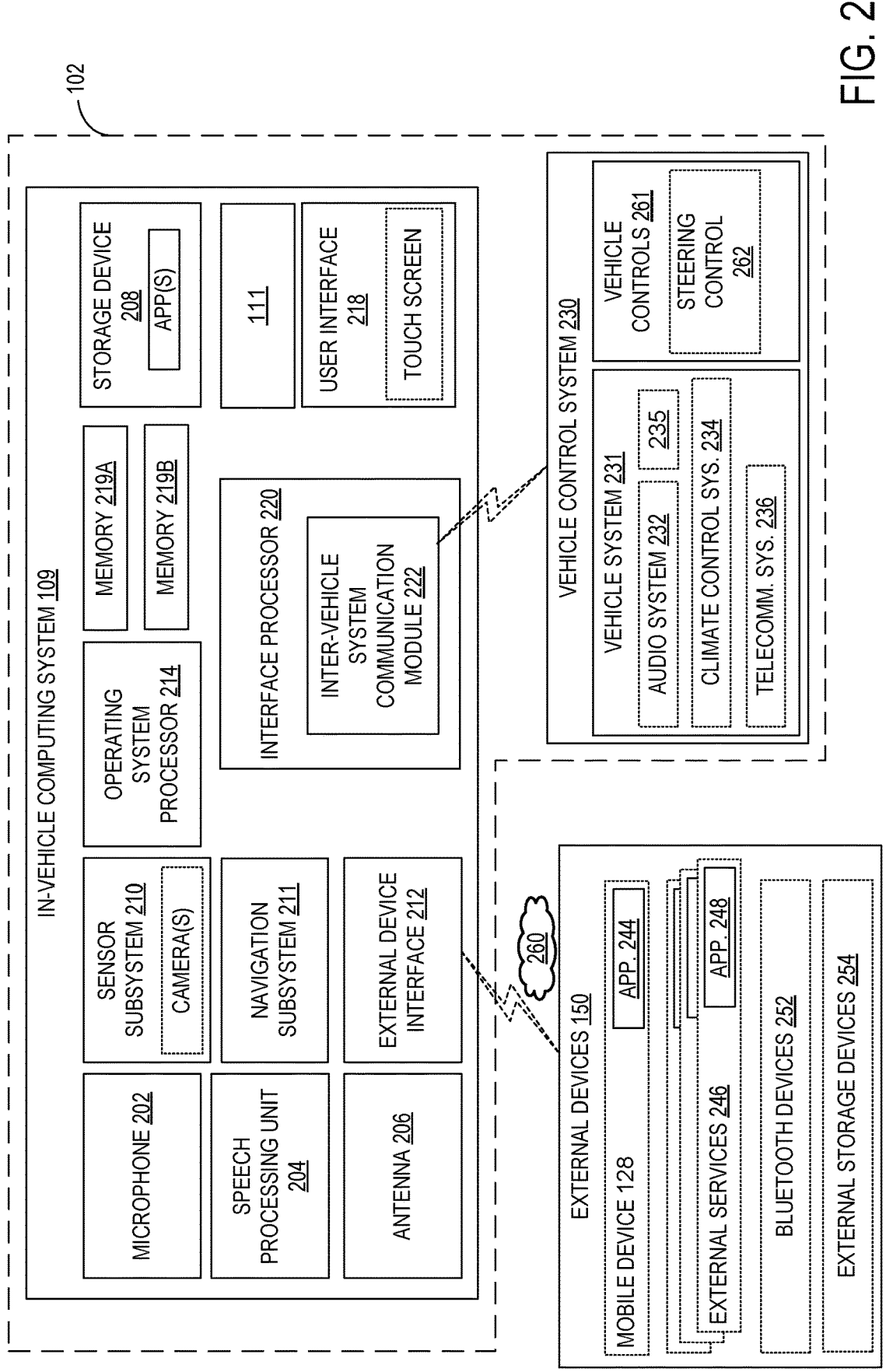
FIG. 2 shows an example in-vehicle computing system in accordance with one or more embodiments of the present disclosure.
Figure 3:
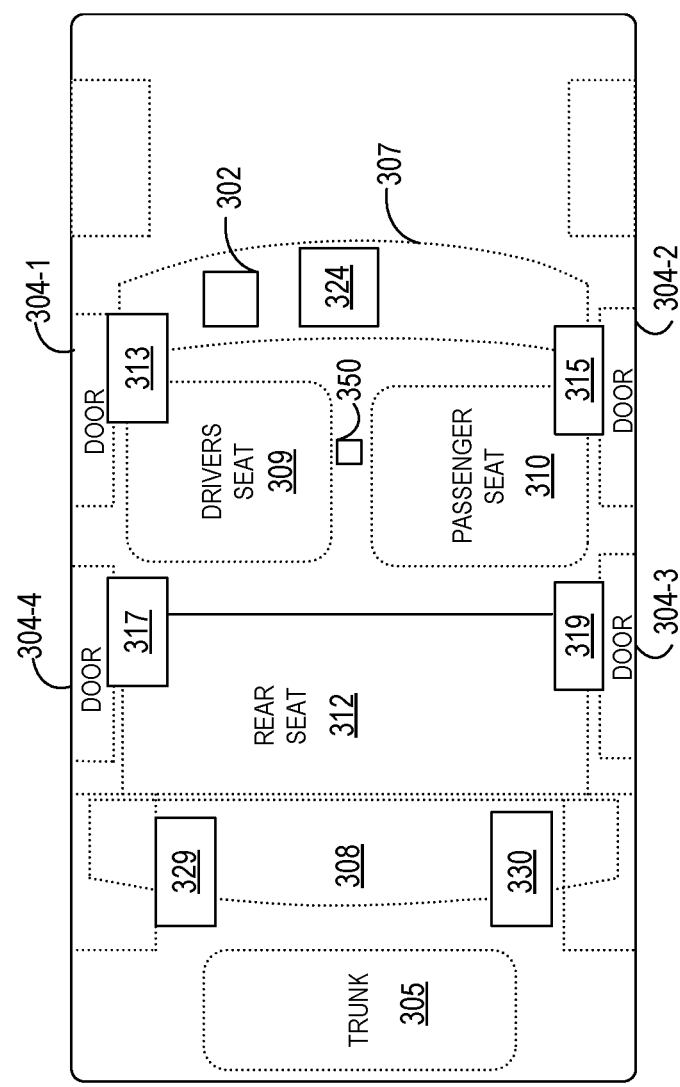
FIG. 3 shows an example sound processing system in a vehicle in accordance with one or more embodiments of the present disclosure.

As shown in FIGS. 1-3, a system according to the present disclosure may be part of a vehicle, and methods according to the present disclosure may be carried out via an in-vehicle computing system.

FIG. 1 shows an example partial view of one type of environment for an audio customization system: an interior of a cabin 100 of a vehicle 102, in which a driver and/or one or more passengers may be seated. Vehicle 102 of FIG. 1 may be a motor vehicle including drive wheels (not shown) and an internal combustion engine 104. Internal combustion engine 104 may include one or more combustion chambers which may receive intake air via an intake passage and exhaust combustion gases via an exhaust passage. Vehicle 102 may be a road automobile, among other types of vehicles. In some examples, vehicle 102 may include a hybrid propulsion system including an energy conversion device operable to absorb energy from vehicle motion and/or the engine and convert the absorbed energy to an energy form suitable for storage by an energy storage device. Vehicle 102 may include a fully electric vehicle, incorporating fuel cells, solar energy capturing elements, and/or other energy storage systems for powering the vehicle.

As shown, an instrument panel 106 may include various displays and controls accessible to a human driver (also referred to as the user) of vehicle 102. For example, instrument panel 106 may include a touch screen 108 of an in-vehicle computing system 109 (e.g., an infotainment system), an audio system control panel, and an instrument cluster 110. Touch screen 108 may receive user input to the in-vehicle computing system 109 for controlling audio output, visual display output, user preferences, control parameter selection, etc. While the example system shown in FIG. 1 includes audio system controls that may be performed via a user interface of in-vehicle computing system 109, such as touch screen 108 without a separate audio system control panel, in other embodiments, the vehicle may include an audio system control panel, which may include controls for a conventional vehicle audio system such as a radio, compact disc player, MP3 player, etc. The audio system controls may include features for controlling one or more aspects of audio output via speakers 112 of a vehicle speaker system. For example, the in-vehicle computing system or the audio system controls may control a volume of audio output, a distribution of sound among the individual speakers of the vehicle speaker system, an equalization of audio signals, and/or any other aspect of the audio output. In further examples, in-vehicle computing system 109 may adjust a radio station selection, a playlist selection, a source of audio input (e.g., from radio or CD or MP3), etc., based on user input received directly via touch screen 108, or based on data regarding the user (such as a physical state and/or environment of the user) received via external devices 150 and/or mobile device 128. The audio system of the vehicle may include an amplifier (not shown) coupled to plurality of loudspeakers (not shown). In some embodiments, one or more hardware elements of in-vehicle computing system 109, such as touch screen 108, a display screen 111, various control dials, knobs and buttons, memory, processor(s), and any interface elements (e.g., connectors or ports) may form an integrated head unit that is installed in instrument panel 106 of the vehicle. The head unit may be fixedly or removably attached in instrument panel 106. In additional or alternative embodiments, one or more hardware elements of the in-vehicle computing system 109 may be modular and may be installed in multiple locations of the vehicle.

The cabin 100 may include one or more sensors for monitoring the vehicle, the user, and/or the environment. For example, the cabin 100 may include one or more seat-mounted pressure sensors configured to measure the pressure applied to the seat to determine the presence of a user, door sensors configured to monitor door activity, humidity sensors to measure the humidity content of the cabin, microphones to receive user input in the form of voice commands, to enable a user to conduct telephone calls, and/or to measure ambient noise in the cabin 100, etc. It is to be understood that the above-described sensors and/or one or more additional or alternative sensors may be positioned in any suitable location of the vehicle. For example, sensors may be positioned in an engine compartment, on an external surface of the vehicle, and/or in other suitable locations for providing information regarding the operation of the vehicle, ambient conditions of the vehicle, a user of the vehicle, etc. Information regarding ambient conditions of the vehicle, vehicle status, or vehicle driver may also be received from sensors external to/separate from the vehicle (that is, not part of the vehicle system), such as sensors coupled to external devices 150 and/or mobile device 128.

Cabin 100 may also include one or more user objects, such as mobile device 128, that are stored in the vehicle before, during, and/or after travelling. The mobile device 128 may include a smart phone, a tablet, a laptop computer, a portable media player, and/or any suitable mobile computing device. The mobile device 128 may be connected to the in-vehicle computing system via communication link 130. The communication link 130 may be wired (e.g., via Universal Serial Bus [USB], Mobile High-Definition Link [MHL], High-Definition Multimedia Interface [HDMI], Ethernet, etc.) or wireless (e.g., via BLUETOOTH, WIFI, WIFI direct, Near-Field Communication [NFC], cellular connectivity, etc.) and configured to provide two-way communication between the mobile device and the in-vehicle computing system. The mobile device 128 may include one or more wireless communication interfaces for connecting to one or more communication links (e.g., one or more of the example communication links described above). The wireless communication interface may include one or more physical devices, such as antenna(s) or port(s) coupled to data lines for carrying transmitted or received data, as well as one or more modules/drivers for operating the physical devices in accordance with other devices in the mobile device. For example, the communication link 130 may provide sensor and/or control signals from various vehicle systems (such as vehicle audio system, climate control system, etc.) and the touch screen 108 to the mobile device 128 and may provide control and/or display signals from the mobile device 128 to the in-vehicle systems and the touch screen 108. The communication link 130 may also provide power to the mobile device 128 from an in-vehicle power source in order to charge an internal battery of the mobile device.

In-vehicle computing system 109 may also be communicatively coupled to additional devices operated and/or accessed by the user but located external to vehicle 102, such as one or more external devices 150. In the depicted embodiment, external devices are located outside of vehicle 102 though it will be appreciated that in alternate embodiments, external devices may be located inside cabin 100. The external devices may include a server computing system, personal computing system, portable electronic device, electronic wrist band, electronic head band, portable music player, electronic activity tracking device, pedometer, smartwatch, GPS system, etc. External devices 150 may be connected to the in-vehicle computing system via communication link 136 which may be wired or wireless, as discussed with reference to communication link 130, and configured to provide two-way communication between the external devices and the in-vehicle computing system. For example, external devices 150 may include one or more sensors and communication link 136 may transmit sensor output from external devices 150 to in-vehicle computing system 109 and touch screen 108. External devices 150 may also store and/or receive information regarding contextual data, user behavior/preferences, operating rules, etc. and may transmit such information from the external devices 150 to in-vehicle computing system 109 and touch screen 108.

In-vehicle computing system 109 may analyze the input received from external devices 150, mobile device 128, and/or other input sources and select settings for various in-vehicle systems (such as climate control system or audio system), provide output via touch screen 108 and/or speakers 112, communicate with mobile device 128 and/or external devices 150, and/or perform other actions based on the assessment. In some embodiments, all or a portion of the assessment may be performed by the mobile device 128 and/or the external devices 150.

In some embodiments, one or more of the external devices 150 may be communicatively coupled to in-vehicle computing system 109 indirectly, via mobile device 128 and/or another of the external devices 150. For example, communication link 136 may communicatively couple external devices 150 to mobile device 128 such that output from external devices 150 is relayed to mobile device 128. Data received from external devices 150 may then be aggregated at mobile device 128 with data collected by mobile device 128, the aggregated data then transmitted to in-vehicle computing system 109 and touch screen 108 via communication link 130. Similar data aggregation may occur at a server system and then transmitted to in-vehicle computing system 109 and touch screen 108 via communication link 136/130.

FIG. 2 shows a block diagram of an in-vehicle computing system 109 configured and/or integrated inside vehicle 102. In-vehicle computing system 109 may perform one or more of the methods described herein in some embodiments. In some examples, the in-vehicle computing system 109 may be a vehicle infotainment system configured to provide information-based media content (audio and/or visual media content, including entertainment content, navigational services, etc.) to a vehicle user to enhance the operator's in-vehicle experience. The vehicle infotainment system may include, or be coupled to, various vehicle systems, subsystems, hardware components, as well as software applications and systems that are integrated in, or integratable into, vehicle 102 in order to enhance an in-vehicle experience for a driver and/or a passenger.

In-vehicle computing system 109 may include one or more processors including an operating system processor 214 and an interface processor 220. Operating system processor 214 may execute an operating system on the in-vehicle computing system, and control input/output, display, playback, and other operations of the in-vehicle computing system. Interface processor 220 may interface with a vehicle control system 230 via an inter-vehicle system communication module 222.

Inter-vehicle system communication module 222 may output data to other vehicle systems 231 and vehicle control elements 261, while also receiving data input from other vehicle components and systems 231, 261, e.g. by way of vehicle control system 230. When outputting data, inter-vehicle system communication module 222 may provide a signal via a bus corresponding to any status of the vehicle, the vehicle surroundings, or the output of any other information source connected to the vehicle. Vehicle data outputs may include, for example, analog signals (such as current velocity), digital signals provided by individual information sources (such as clocks, thermometers, location sensors such as Global Positioning System [GPS] sensors, etc.), digital signals propagated through vehicle data networks (such as an engine CAN bus through which engine related information may be communicated, a climate control CAN bus through which climate control related information may be communicated, and a multimedia data network through which multimedia data is communicated between multimedia components in the vehicle). For example, the in-vehicle computing system 109 may retrieve from the engine CAN bus the current speed of the vehicle estimated by the wheel sensors, a power state of the vehicle via a battery and/or power distribution system of the vehicle, an ignition state of the vehicle, etc. In addition, other interfacing means such as Ethernet may be used as well without departing from the scope of this disclosure.

A non-volatile storage device 208 may be included in in-vehicle computing system 109 to store data such as instructions executable by processors 214 and 220 in non-volatile form. The storage device 208 may store application data, including prerecorded sounds, to enable the in-vehicle computing system 109 to run an application for connecting to a cloud-based server and/or collecting information for transmission to the cloud-based server. The application may retrieve information gathered by vehicle systems/sensors, input devices (e.g., user interface 218), data stored in volatile 219A or non-volatile storage device (e.g., memory) 219B, devices in communication with the in-vehicle computing system (e.g., a mobile device connected via a Bluetooth link), etc. In-vehicle computing system 109 may further include a volatile memory 219A. Volatile memory 219A may be random access memory (RAM). Non-transitory storage devices, such as non-volatile storage device 208 and/or non-volatile memory 219B, may store instructions and/or code that, when executed by a processor (e.g., operating system processor 214 and/or interface processor 220), controls the in-vehicle computing system 109 to perform one or more of the actions described in the disclosure.

A microphone 202 may be included in the in-vehicle computing system 109 to receive voice commands from a user, to measure ambient noise in the vehicle, to determine whether audio from speakers of the vehicle is tuned in accordance with an acoustic environment of the vehicle, etc. A speech processing unit 204 may process voice commands, such as the voice commands received from the microphone 202. In some embodiments, in-vehicle computing system 109 may also be able to receive voice commands and sample ambient vehicle noise using a microphone included in an audio system 232 of the vehicle.

One or more additional sensors may be included in a sensor subsystem 210 of the in-vehicle computing system 109. For example, the sensor subsystem 210 may include a camera, such as a rear view camera for assisting a user in parking the vehicle and/or a cabin camera for identifying a user (e.g., using facial recognition and/or user gestures). Sensor subsystem 210 of in-vehicle computing system 109 may communicate with and receive inputs from various vehicle sensors and may further receive user inputs. For example, the inputs received by sensor subsystem 210 may include transmission gear position, transmission clutch position, gas pedal input, brake input, transmission selector position, vehicle speed, engine speed, mass airflow through the engine, ambient temperature, intake air temperature, etc., as well as inputs from climate control system sensors (such as heat transfer fluid temperature, antifreeze temperature, fan speed, passenger compartment temperature, desired passenger compartment temperature, ambient humidity, etc.), an audio sensor detecting voice commands issued by a user, a fob sensor receiving commands from and optionally tracking the geographic location/proximity of a fob of the vehicle, etc. While certain vehicle system sensors may communicate with sensor subsystem 210 alone, other sensors may communicate with both sensor subsystem 210 and vehicle control system 230, or may communicate with sensor subsystem 210 indirectly via vehicle control system 230. A navigation subsystem 211 of in-vehicle computing system 109 may generate and/or receive navigation information such as location information (e.g., via a GPS sensor and/or other sensors from sensor subsystem 210), route guidance, traffic information, point-of-interest (POI) identification, and/or provide other navigational services for the driver.

External device interface 212 of in-vehicle computing system 109 may be coupleable to and/or communicate with one or more external devices 150 located external to vehicle 102. While the external devices are illustrated as being located external to vehicle 102, it is to be understood that they may be temporarily housed in vehicle 102, such as when the user is operating the external devices while operating vehicle 102. In other words, the external devices 150 are not integral to vehicle 102. The external devices 150 may include a mobile device 128 (e.g., connected via a Bluetooth, NFC, WIFI direct, or other wireless connection) or an alternate Bluetooth-enabled device 252. Mobile device 128 may be a mobile phone, smart phone, wearable devices/sensors that may communicate with the in-vehicle computing system via wired and/or wireless communication, or other portable electronic device(s). Other external devices include external services 246. For example, the external devices may include extra-vehicular devices that are separate from and located externally to the vehicle. Still other external devices include external storage devices 254, such as solid-state drives, pen drives, USB drives, etc. External devices 150 may communicate with in-vehicle computing system 109 either wirelessly or via connectors without departing from the scope of this disclosure. For example, external devices 150 may communicate with in-vehicle computing system 109 through the external device interface 212 over network 260, a universal serial bus (USB) connection, a direct wired connection, a direct wireless connection, and/or other communication link.

The external device interface 212 may provide a communication interface to enable the in-vehicle computing system to communicate with mobile devices associated with contacts of the driver. For example, the external device interface 212 may enable phone calls to be established and/or text messages (e.g., SMS, MMS, etc.) to be sent (e.g., via a cellular communications network) to a mobile device associated with a contact of the driver. The external device interface 212 may additionally or alternatively provide a wireless communication interface to enable the in-vehicle computing system to synchronize data with one or more devices in the vehicle (e.g., the driver's mobile device) via WIFI direct, as described in more detail below.

One or more applications 244 may be operable on mobile device 128. As an example, mobile device application 244 may be operated to aggregate user data regarding interactions of the user with the mobile device. For example, mobile device application 244 may aggregate data regarding music playlists listened to by the user on the mobile device, telephone call logs (including a frequency and duration of telephone calls accepted by the user), positional information including locations frequented by the user and an amount of time spent at each location, etc. The collected data may be transferred by application 244 to external device interface 212 over network 260. In addition, specific user data requests may be received at mobile device 128 from in-vehicle computing system 109 via the external device interface 212. The specific data requests may include requests for determining where the user is geographically located, an ambient noise level and/or music genre at the user's location, an ambient weather condition (temperature, humidity, etc.) at the user's location, etc. Mobile device application 244 may send control instructions to components (e.g., microphone, amplifier etc.) or other applications (e.g., navigational applications) of mobile device 128 to enable the requested data to be collected on the mobile device or requested adjustment made to the components. Mobile device application 244 may then relay the collected information back to in-vehicle computing system 109.

Likewise, one or more applications 248 may be operable on external services 246. As an example, external services applications 248 may be operated to aggregate and/or analyze data from multiple data sources. For example, external services applications 248 may aggregate data from one or more social media accounts of the user, data from the in-vehicle computing system (e.g., sensor data, log files, user input, etc.), data from an internet query (e.g., weather data, POI data), etc. The collected data may be transmitted to another device and/or analyzed by the application to determine a context of the driver, vehicle, and environment and perform an action based on the context (e.g., requesting/sending data to other devices).

Vehicle control system 230 may include controls for controlling aspects of various vehicle systems 231 involved in different in-vehicle functions. These may include, for example, controlling aspects of vehicle audio system 232 for providing audio entertainment to the vehicle occupants, aspects of climate control system 234 for meeting the cabin cooling or heating needs of the vehicle occupants, as well as aspects of telecommunication system 236 for enabling vehicle occupants to establish telecommunication linkage with others.

Audio system 232 may include one or more acoustic reproduction devices including electromagnetic transducers such as speakers 235. Vehicle audio system 232 may be passive or active such as by including a power amplifier. In some examples, in-vehicle computing system 109 may be the only audio source for the acoustic reproduction device or there may be other audio sources that are connected to the audio reproduction system (e.g., external devices such as a mobile phone). The connection of any such external devices to the audio reproduction device may be analog, digital, or any combination of analog and digital technologies.

Climate control system 234 may be configured to provide a comfortable environment within the cabin or passenger compartment of vehicle 102. Climate control system 234 includes components enabling controlled ventilation such as air vents, a heater, an air conditioner, an integrated heater and air-conditioner system, etc. Other components linked to the heating and air-conditioning setup may include a windshield defrosting and defogging system capable of clearing the windshield and a ventilation-air filter for cleaning outside air that enters the passenger compartment through a fresh-air inlet.

Vehicle control system 230 may also include controls for adjusting the settings of various vehicle controls 261 (or vehicle system control elements) related to the engine and/or auxiliary elements within a cabin of the vehicle, such as steering wheel controls 262 (e.g., steering wheel-mounted audio system controls, cruise controls, windshield wiper controls, headlight controls, turn signal controls, etc.), instrument panel controls, microphone(s), accelerator/brake/clutch pedals, a gear shift, door/window controls positioned in a driver or passenger door, seat controls, cabin light controls, audio system controls, cabin temperature controls, etc. Vehicle controls 261 may also include internal engine and vehicle operation controls (e.g., engine controller module, actuators, valves, etc.) that are configured to receive instructions via the CAN bus of the vehicle to change operation of one or more of the engine, exhaust system, transmission, and/or other vehicle system. The control signals may also control audio output at one or more speakers 235 of the vehicle's audio system 232. For example, the control signals may adjust audio output characteristics such as volume, equalization, audio image (e.g., the configuration of the audio signals to produce audio output that appears to a user to originate from one or more defined locations), audio distribution among a plurality of speakers, etc. Likewise, the control signals may control vents, air conditioner, and/or heater of climate control system 234. For example, the control signals may increase delivery of cooled air to a specific section of the cabin.

Control elements positioned on an outside of a vehicle (e.g., controls for a security system) may also be connected to computing system 109, such as via communication module 222. The control elements of the vehicle control system may be physically and permanently positioned on and/or in the vehicle for receiving user input. In addition to receiving control instructions from in-vehicle computing system 109, vehicle control system 230 may also receive input from one or more external devices 150 operated by the user, such as from mobile device 128. This allows aspects of vehicle systems 231 and vehicle controls 261 to be controlled based on user input received from the external devices 150.

In-vehicle computing system 109 may further include an antenna 206. Antenna 206 is shown as a single antenna, but may comprise one or more antennas in some embodiments. The in-vehicle computing system may obtain broadband wireless internet access via antenna 206, and may further receive broadcast signals such as radio, television, weather, traffic, and the like. The in-vehicle computing system may receive positioning signals such as GPS signals via one or more antennas 206. The in-vehicle computing system may also receive wireless commands via FR such as via antenna(s) 206 or via infrared or other means through appropriate receiving devices. In some embodiments, antenna 206 may be included as part of audio system 232 or telecommunication system 236. Additionally, antenna 206 may provide AM/FM radio signals to external devices 150 (such as to mobile device 128) via external device interface 212.

One or more elements of the in-vehicle computing system 109 may be controlled by a user via user interface 218. User interface 218 may include a graphical user interface presented on a touch screen, such as touch screen 108 of FIG. 1, and/or user-actuated buttons, switches, knobs, dials, sliders, etc. For example, user-actuated elements may include steering wheel controls, door and/or window controls, instrument panel controls, audio system settings, climate control system settings, and the like. A user may also interact with one or more applications of the in-vehicle computing system 109 and mobile device 128 via user interface 218. In addition to receiving a user's vehicle setting preferences on user interface 218, vehicle settings selected by in-vehicle control system may be displayed to a user on user interface 218. Notifications and other messages (e.g., received messages), as well as navigational assistance, may be displayed to the user on a display of the user interface. User preferences/information and/or responses to presented messages may be performed via user input to the user interface.

FIG. 3 is a block diagram of a vehicle 102 that includes an example audio or sound processing system (AS) 302, which may include any or a combination of the sound processing systems and methods described below. The vehicle 102 includes doors 304, a driver seat 309, a passenger seat 310, and a rear seat 312. While a four-door vehicle is shown including doors 304-1, 304-2, 304-3, and 304-4, the audio system (AS) 102 may be used in vehicles having more or fewer doors. The vehicle 102 may be an automobile, truck, boat, or the like. Although only one rear seat is shown, larger vehicles may have multiple rows of rear seats. Smaller vehicles may have only one or more seats. While a particular example configuration is shown, other configurations may be used including those with fewer or additional components.

The audio system 302 (which may include an amplifier and/or other audio processing device for receiving, processing, and/or outputting audio to one or more speakers of the vehicle) may improve the spatial characteristics of surround sound systems. The audio system 302 supports the use of a variety of audio components such as radios, COs, DVDs, their derivatives, and the like. The audio system 302 may use 2-channel source material such as direct left and right, 5.1 channel, 6.2 channel, 7 channel, 12 channel and/or any other source materials from a matrix decoder digitally encoded/decoded discrete source material, and the like. The audio system 302 utilizes a channel that is only for TI/HWL sounds and is separate from a channel/s for remaining sounds, including one or more of remaining warning, media, navigational, and telephone/telematics sounds.

The amplitude and phase characteristics of the source material and the reproduction of specific sound field characteristics in the listening environment both play a key role in the successful reproduction of a surround sound field.

The audio system 302 may improve the reproduction of a surround sound field by controlling the sound delay time, surround upmixer parameters (e.g., wrap, reverb room size, etc.), amplitude, phase, and mixing ratio between discrete and passive decoder surround signals and/or the direct two-channel output signals, in at least one example. The amplitude, phase, and mixing ratios may be controlled between the discrete and passive decoder output signals. The spatial sound field reproduction may be improved for all seating locations by re-orientation of the direct, passive, and active mixing and steering parameters, especially in a vehicle environment.

The mixing and steering ratios as well as spectral characteristics may be adaptively modified as a function of the noise and other environmental factors. In a vehicle, information from the data bus, microphones, and other transduction devices may be used to control the mixing and steering parameters.

The vehicle 102 has a front center speaker (CTR speaker) 324, a front left speaker (FL speaker) 313, a front right speaker (FR speaker) 315, and at least one pair of surround speakers.

The surround speakers may be a left side speaker (LS speaker) 317 and a right side speaker (RS speaker) 319, a left rear speaker (LR speaker) 329 and a right rear speaker (RR speaker) 330, or a combination of speaker sets. Other speaker sets may be used. While not shown, one or more dedicated subwoofers or other drivers may be present. Possible subwoofer mounting locations include the trunk 305, below a seat, or the rear shelf 308. The vehicle 102 may also have one or more microphones 350 mounted in the interior.

Each CTR speaker, FL speaker, FR speaker, LS speaker, RS speaker, LR speaker, and RR speaker may include one or more transducers of a predetermined range of frequency response such as a tweeter, a mid-range, or a woofer. The tweeter, mid-range, or woofer may be mounted adjacent to each other in essentially the same location or in different locations. For example, the FL speaker 313 may be a tweeter located in door 304-1 or elsewhere at a height roughly equivalent to a side mirror or higher. The FR speaker 315 may have a similar arrangement to FL speaker 313 on the right side of the vehicle (e.g., in door 304-2).

The LR speaker 329 and the RR speaker 330 may each be a woofer mounted in the rear shelf 308. The CTR speaker 324 may be mounted in the front dashboard 307, in the roof, on or near the rear-view mirror, or elsewhere in the vehicle 102. In other examples, other configurations of loudspeakers with other frequency response ranges are possible. In some embodiments, additional speakers may be added to an upper pillar in the vehicle to enhance the height of the sound image. For example, an upper pillar may include a vertical or near-vertical support of a car's window area. In some examples, the additional speakers may be added to an upper region of an "A" pillar toward a front of the vehicle.

Figure 4A:
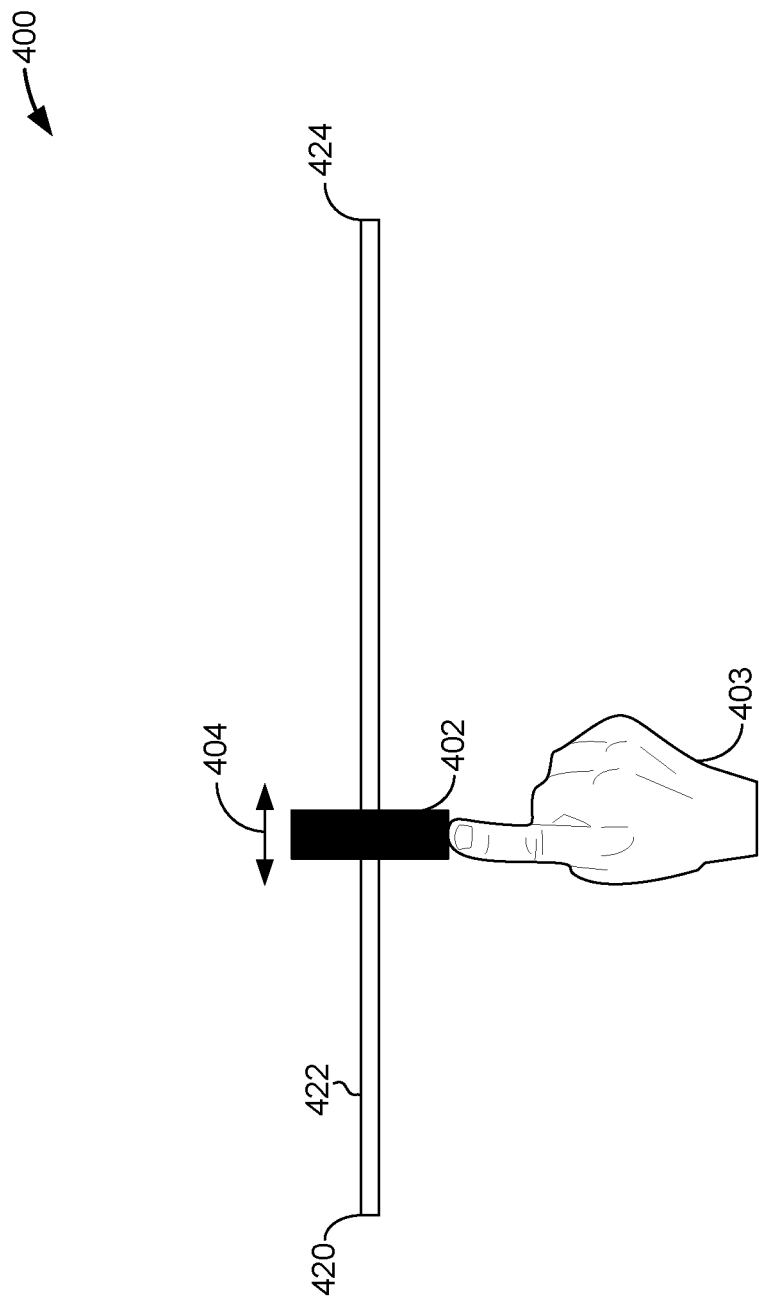
FIG. 4A shows a schematic depiction of an example activity control.

Turning now to FIG. 4A, one example of an activity control 400 is shown. The activity control 400 may be displayed on a touch screen (e.g., 108 of FIG. 1) or mobile device 128. Alternatively, activity control 400 may be realized as a three dimensional device that is part of audio system 232 of FIG. 2. In this example, activity control 400 takes a form of a slider control that includes a slider bar 402 and a slide bar guide 422. However, in other examples, activity control 400 may be realized in the form of a rotary knob or other known user input device without departing from the scope or intent of the present description. A position or state of activity control 400 may refer to a position or state of slider bar 402.

Slider bar 402 may be moved longitudinally along the length of slide bar guide 422 as indicated by arrows 404 by human user 403. Slider bar 402 may be moved to a left extent 420 or a right extent 424 to adjust sound activity that may be associated with a particular scene that may be shown via display 111 of FIG. 1. For example, a user may wish to relax by listening to prerecorded sounds of rain falling, waves crashing on a seashore, or water rushing down a creek. The user may select which sound to play back over vehicle speakers and a visual representation of the sound may be displayed on a display panel. Attributes of the sound that is selected for playback over vehicle speakers may be adjusted according to a position of slider bar 402, or of an operating state of the activity control, as described in further detail in the descriptions of FIGS. 4B-6.

Slider bar 402 may be in a base position when it is moved left to extent 420. Slider bar 402 may be fully advanced when it is moved right to extent 424. In one example, lowest level outputs of controlled sounds or features may be output when slider bar 402 is positioned at the left extent 420. Greatest or highest level outputs of controlled sounds or features may be output when slider bar 402 is positioned at the right extent 424.

Figure 4B:
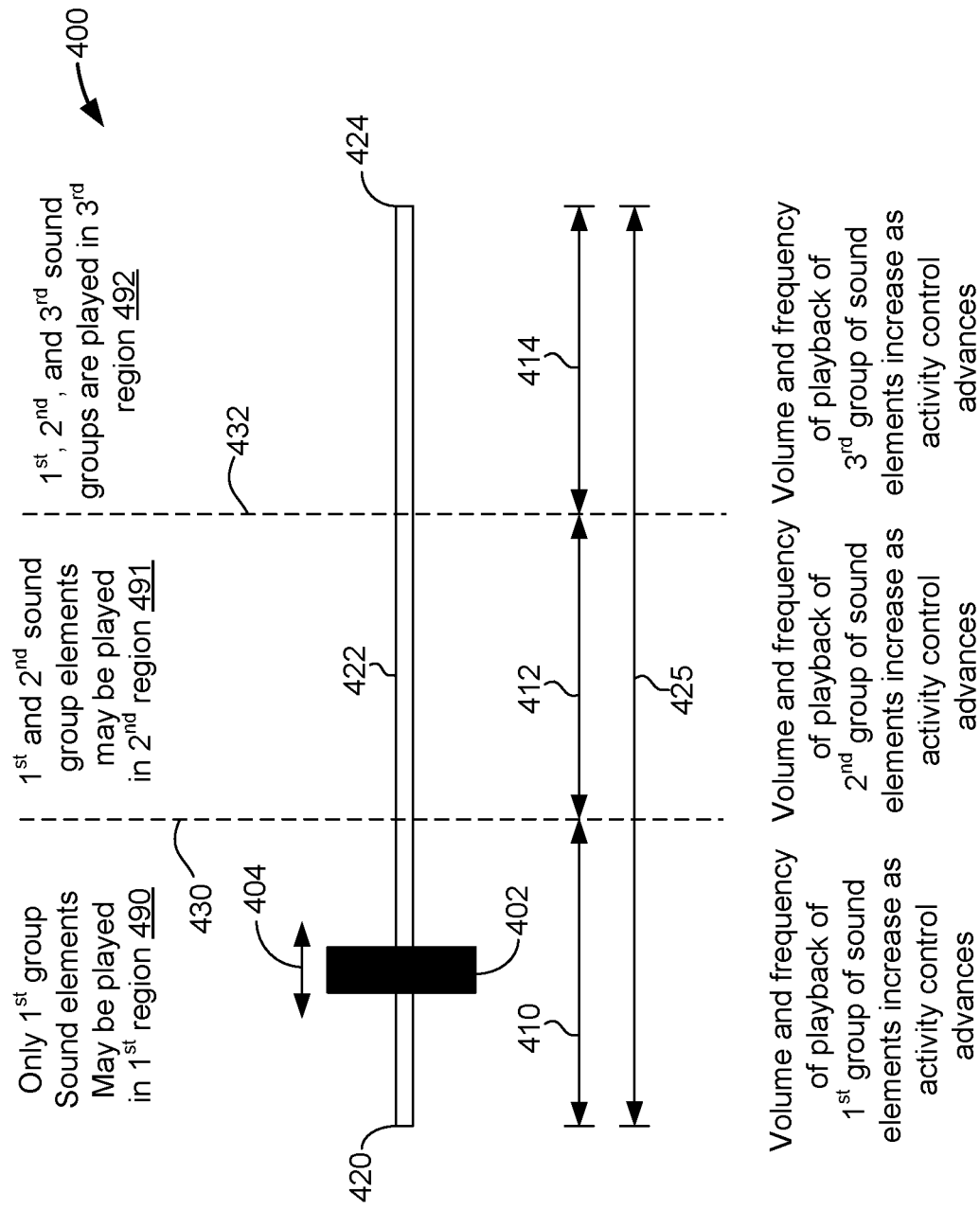
FIG. 4B shows a schematic depiction of an activity control with example control regions.

Referring now to FIG. 4B, an activity control 400 that includes a plurality of control regions is shown. In this example, activity control 400 includes three control regions; however, in other examples, the actual total number of control regions may be greater than three or less than three. Further, in this example, the control regions each comprise about one third of the length of slide bar guide 422, but the control regions may be adjusted according to other dimensions, if desired. The control range or range of authority of activity control 400 is indicated by arrow 425 and it spans the three control regions.

A first control region 490 for slide bar 402 begins at a left extent 420 of slide bar guide 422 and it ends at vertical line 430. Leader 410 shows the range of first control region 490. Slide bar 402 is shown in the first control region 490, so the computing system 109 shown in FIG. 1 or audio system 232 shown in FIG. 2 may play back sounds digitally stored in non-volatile memory that are included in a first group of sounds that are associated with a particular theme, scene, or scenescape that has been selected by a user. A theme may be a mood or state of mind that is being conveyed (e.g., relax, high emotional energy, be happy, etc.). The sounds may be played back or broadcast through the vehicle's speakers. The first group of sounds may be characterized as steady-state sounds. Steady-state sounds may include but are not limited to the sound of falling rain drops, the sound of waves crashing on a seashore, the sound of crickets softly chirping, the sound of a soft breeze, and other sounds intended to capture the essence of a mode or the selected theme, scene, or scenescape. Steady-state sounds may be perceived by users as being continuous.

The position of slide bar 402 within the first control region 490 may define the volume or sound power output level of the speakers and the frequency of playback or density for the steady-state sounds that are included in the selected scene or scenescape. For example, if the slide bar is positioned at the left extent of slide bar guide 422, then steady-state sounds in the selected theme, scene, or scenescape may be played back at a low frequency of repetition (e.g., a rain falling sound sequence retrieved from memory may repeat at a rate of 0.03 Hz) and a very low volume or sound power output level. If the slide bar 402 is moved to the right and stopped before the slide bar enters the second control region 491, then the same steady-state sounds may be played back at a higher frequency (e.g., 0.1 Hz) and a low volume or sound power level. Thus, as slide bar 402 is moved from left to right while in the first control region, the amount of sound power and frequency of playback of steady-state sounds is increased.

A second control region 491 for slide bar 402 begins at the vertical line 430 and it ends at vertical line 432. Leader 412 shows the range of second control region 491. In one example, when slide bar 402 enters the second control region 491, the volume or sound power output of steady-state sounds is maintained at its most recent level and the stead-state sounds frequency of playback is maintained at its most recent level. The computing system 109 shown in FIG. 1 or audio system 232 shown in FIG. 2 may begin to play back sounds stored in non-volatile memory that are included in a second group of sounds that are associated with the selected particular theme, scene, or scenescape. The sounds may be played back or broadcast through the vehicle's speakers. The second group of sounds may be characterized as dynamic sounds. Dynamic sounds may include but are not limited to the sound birds calling, the sound of distant thunder, the sound of owls hooting, and similar sounds emulating the wildlife and fauna included in the selected theme, scene, or scenescape. Dynamic sounds may have a perceived characteristic of not being continuous.

The position of slide bar 402 within the second control region 491 may define the volume or sound power output level of the speakers and the frequency of playback or density for the dynamic sounds that are included in the selected theme, scene, or scenescape. For example, if the slide bar 402 is positioned just to the right of line 430, then steady-state sounds in the selected theme, scene, or scenescape may be played back at their frequency of repetition and volume or sound power output when slide bar 402 reached the positon of line 430. The dynamic sounds in the selected theme, scene, or scenescape may be played back at a low frequency of repletion and a low volume or sound power output when slide bar 402 is positioned just to the right of line 430.

If the slide bar 402 is moved to the right and stopped just before the slide bar reaches a position of vertical line 432, then steady-state sounds in the selected theme, scene, or scenescape may continue to be played back at their frequency of repetition and volume or sound power output when slide bar 402 reached the positon of line 430. The dynamic sounds in the selected theme, scene, or scenescape may be played back at a higher frequency of repletion and a higher volume or sound power output than when slide bar 402 is positioned just to the left of line 430.

A third control region 492 for slide bar 402 begins at the vertical line 432 and it ends at the right extent 424 of slide bar guide 422. Leader 414 shows the range of third control region 492. In one example, when slide bar 402 enters the third control region 492, the volume or sound power output of steady-state sounds and dynamic sounds may be maintained at their most recent levels and the stead-state and dynamic sounds frequency of playback may be maintained at their most recent levels. The computing system 109 shown in FIG. 1 or audio system 232 shown in FIG. 2 may begin to play back sounds stored in non-volatile memory that are included in a third group of sounds that are associated with the selected particular theme, scene, or scenescape. The sounds may be played back or broadcast through the vehicle's speakers. The third group of sounds may be characterized as surreal sound elements. Surreal sound elements may include but are not limited to the sound of coyotes howling, the sound of elk bugling, the sound of thunder claps, and other unnatural sounds intended to augment the user's emotional response to the selected theme, scene, or scenescape.

The position of slide bar 402 within the third control region 492 may define the volume or sound power output level of the speakers and the frequency of playback or density for the surreal sounds that are included in the selected theme, scene, or scenescape. For example, if the slide bar 402 is positioned just to the right of line 432, then steady-state and dynamic sounds in the selected theme, scene, or scenescape may be played back at their frequency of repetition and volume or sound power output when slide bar 402 reached the positon of line 432. The surreal sounds in the selected theme, scene, or scenescape may be played back at a low frequency of repletion and a low volume or sound power output when slide bar 402 is positioned just to the right of line 432.

If the slide bar 402 is moved to the right and stopped just before the slide bar reaches the extent 424 of slide bar guide 422, then steady-state and dynamic sounds in the selected theme, scene, or scenescape may continue to be played back at their frequency of repetition and volume or sound power output when slide bar 402 reached the positon of line 432. The surreal sounds in the selected theme, scene, or scenescape may be played back at a higher frequency of repletion and a higher volume or sound power output than when slide bar 402 is positioned just to the right of line 432.

Thus, a sole activity control may be the basis for increasing a complexity of sounds generated via computing system 109 shown in FIG. 1 or audio system 232 shown in FIG. 2. Further, the volume and intensity of sound generated and broadcast through speakers may be adjusted via the same activity control by defining control regions for the activity control.

Figure 4C:
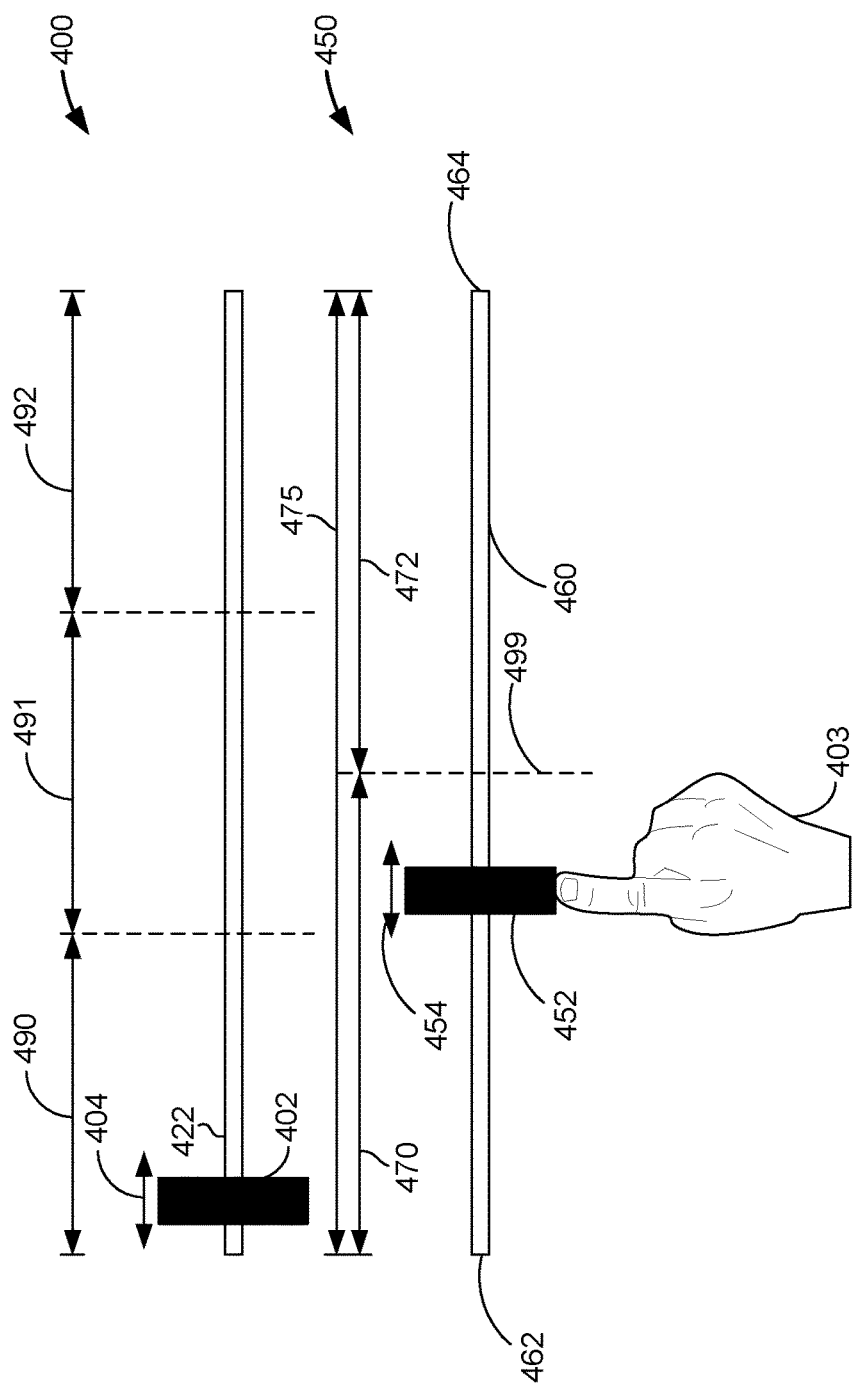
FIG. 4C shows a schematic depiction of two activity controls with example control regions.

Referring now to FIG. 4C, an example where two activity controls are included in the system of FIGS. 1-3 is shown. Activity control 400 is the same activity control that is shown in FIGS. 4A and 4B. Further, activity control 400 includes the same previously mentioned control regions 490-492. Activity control 400 also includes the same slide bar 402 and slide bar guide 422. Activity control 400 may operate and provide the functionality previously described.

Second activity control 450 includes a slide bar 452 and a slide bar guide 460. The slide bar 452 may be moved longitudinally left and right along slide bar guide 460 and between left extent 462 and right extent 464 as indicated by arrows 454 via user 403. In this example, second activity control 450 has a control range or range of authority 475 that is subdivided into two control regions 470 and 472, although range of authority 475 may be subdivided into additional control regions if desired. In one example, surround sound control parameters may be adjusted as a function of a position of slide bar 452 and the control region in which slide bar 452 is located. For example, when slide bar 452 is positioned in first control region 470 a center spread may be increased as slide bar 452 is moved from extent 462 toward vertical line 499. Increasing the center spread may change sound distribution from a center speaker to front left and right speakers. The center spread may reach a maximum level when slide bar 452 reaches the position of vertical line 499. If slide bar moves into second control region 472, then the level of up-mixed channels may be adjusted. For example, the level of up-mixed channels may increase as slide bar 452 moves from vertical line 499 to extent 464. Second activity control 450 may also adjust other surround sound control parameters such as room size emulation, delay time, and dynamic compression. Further, second activity control 450 may adjust sound control parameters for vehicle specific sound control parameters. For example, second activity control 450 may adjust delivery of sounds to speakers to improve sound reception for a particular passenger (e.g., front driver, front passenger, etc.).

In an example, the second activity control 450 may adjust the location of specific sound to different regions of the vehicle. For example, the second activity control may adjust the sound distribution and/or location within the various vehicle zones (e.g., front left passenger, front right passenger, etc.) differently for the different sound group regions, such as steady-state sound elements, dynamic sound elements, and/or surreal sound elements. The user input controls may thus provide for adjustment of the vehicle zone to provide different control of each of the different group regions in each of the vehicle zones. In another example, the user input controls may provide for movement from one region to another of only one of the group regions, such as the steady-state sound element.

Thus, activity controls may be assigned to adjust more than one sound control parameter. Further, two or more activity controls may be provided to further increase system flexibility and user experience. In this way, a single activity control may be assigned one or more functions to reduce a number of user inputs, thereby reducing system complexity as perceived by a user.

The system of FIGS. 1-4C provides for a sound system of a vehicle, comprising: one or more speakers; and a controller electrically coupled to the one or more speakers including executable instructions stored in non-transitory memory that cause the controller to increase a frequency of occurrence and audible level of a sound that is generated via the one or more speakers according to a state of a user control. The system includes wherein the user control includes an operating range that is subdivided into a plurality of sound group regions, each of the plurality of sound group regions including one or more sounds unique to a sound group region with the plurality of sound group regions, and wherein the one or more speakers are included within a vehicle passenger cabin. The system further comprises additional executable instructions to generate sounds from only a first group of sounds included in a first sound group region of the plurality of sound group regions when a user control is positioned in the first sound group region. The system further comprises additional executable instructions to generate sounds from only from the first group of sounds and a second group of sounds included in first and second sound group regions of the plurality of sound group regions when the user control is positioned in the second sound group region. The system further comprises additional executable instructions to generate sounds from a first group of sounds, the second group of sounds, and the third group of sounds when the user control is positioned in the third sound group region. The system further comprises additional executable instructions to increase a sound level of sounds generated according to the position of the user control.

Figure 5:
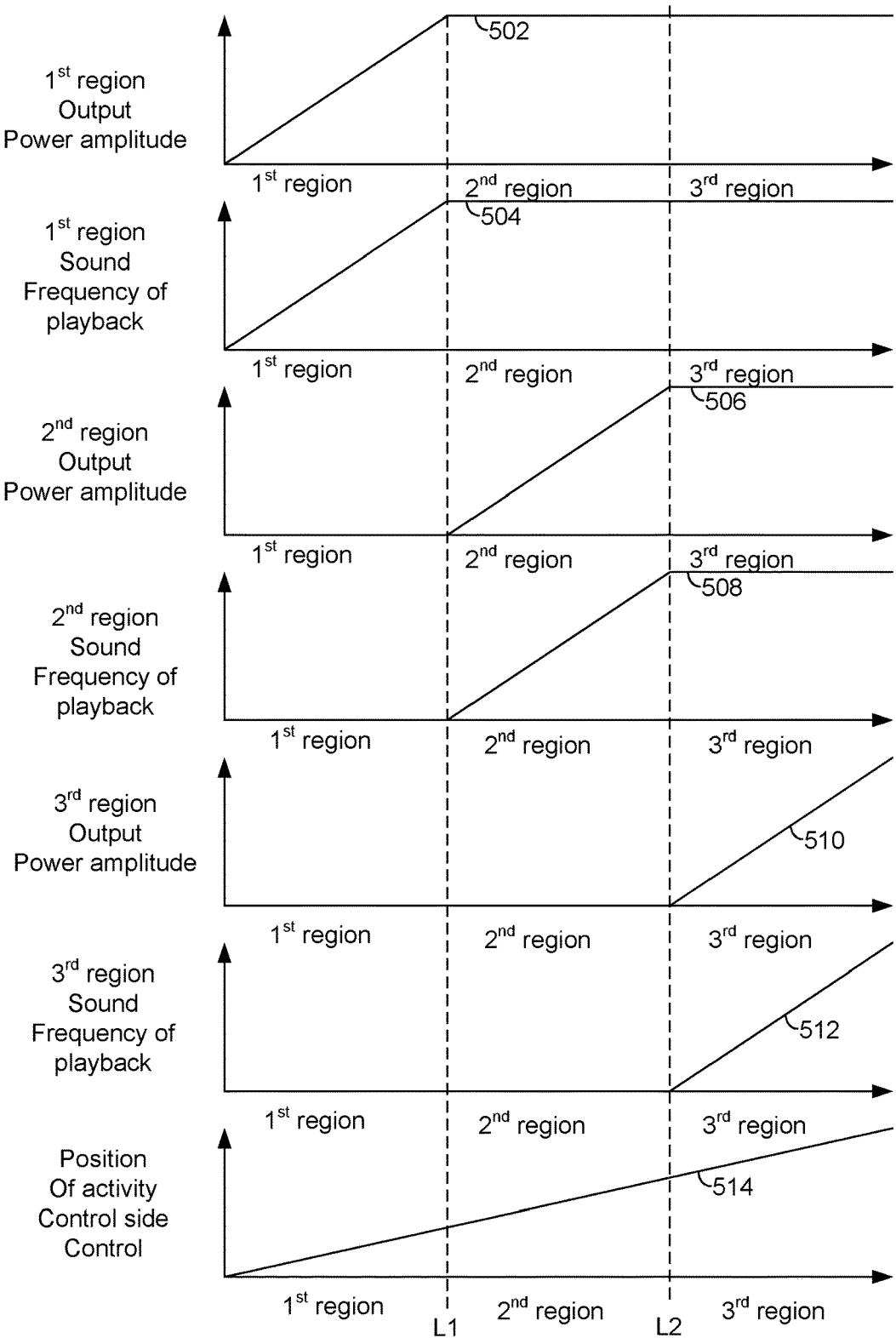
FIG. 5 shows plots of audio attributes that may be modified according to a state of the user interface shown in FIG. 4.

Referring now to FIG. 5, plots showing how audio attributes of sounds may be modified according to a state of an activity control or user interface changes are shown. The plots show how a computing system 109 shown in FIG. 1 or an audio system 232 shown in FIG. 2 may adjust sounds according to the method of FIG. 6 and the system of FIGS. 1-4A.

The first plot from the top of FIG. 5 is a plot of sound output power amplitude or volume versus activity control regions (e.g., 490-492). The vertical axis represents the sound output power amplitude for sounds that are included in a first group (e.g., steady-state sounds) of sounds that are associated with a first control region of the activity control. The sound output power amplitude increases in the direction of the vertical axis arrow. The horizontal axis represents activity control regions and it is broken into three regions as shown in FIG. 4B. Trace 502 represents the sound output power amplitude or volume for sounds included in the first group of sounds.

The second plot from the top of FIG. 5 is a plot of sound frequency of playback (e.g., the frequency a sound is repeated when broadcast via speakers) for sounds that are included in the first group of sounds versus activity control regions. The vertical axis represents the frequency of playback for sounds that are included in a first group of sounds that are associated with a first control region of the activity control. The horizontal axis represents activity control regions and it is broken into three regions as shown in FIG. 4B. Trace 504 represents the sound frequency of playback for sounds included in the first group of sounds.

The third plot from the top of FIG. 5 is a plot of sound output power amplitude or volume versus activity control regions. The vertical axis represents the sound output power amplitude for sounds that are included in a second group (e.g., dynamic sounds) of sounds that are associated with a second control region of the activity control. The sound output power amplitude increases in the direction of the vertical axis arrow. The horizontal axis represents activity control regions and it is broken into three regions as shown in FIG. 4B. Trace 506 represents the sound output power amplitude or volume for sounds included in the second group of sounds.

The fourth plot from the top of FIG. 5 is a plot of sound frequency of playback for sounds that are included in the second group of sounds versus activity control regions. The vertical axis represents the frequency of playback for sounds that are included in a second group of sounds that are associated with a second control region of the activity control. The horizontal axis represents activity control regions and it is broken into three regions as shown in FIG. 4B. Trace 508 represents the sound frequency of playback for sounds included in the second group of sounds.

The fifth plot from the top of FIG. 5 is a plot of sound output power amplitude or volume versus activity control regions. The vertical axis represents the sound output power amplitude for sounds that are included in a third group (e.g., surreal sounds) of sounds that are associated with a third control region of the activity control. The sound output power amplitude increases in the direction of the vertical axis arrow. The horizontal axis represents activity control regions and it is broken into three regions as shown in FIG. 4B. Trace 510 represents the sound output power amplitude or volume for sounds included in the third group of sounds.

The sixth plot from the top of FIG. 5 is a plot of sound frequency of playback for sounds that are included in the third group of sounds versus activity control regions. The vertical axis represents the frequency of playback for sounds that are included in a third group of sounds that are associated with a third control region of the activity control. The horizontal axis represents activity control regions and it is broken into three regions as shown in FIG. 4B. Trace 512 represents the sound frequency of playback for sounds included in the third group of sounds.

The seventh plot from the top of FIG. 5 is a plot of activity control state or position versus activity control regions. The vertical axis represents the state or position of the activity control (e.g., slide bar 402) and the activity control moves from left to right in the direction of the vertical axis arrow. The horizontal axis represents activity control regions and it is broken into three regions as shown in FIG. 4B. Trace 514 represents the activity control state or position.

At the left most side of the plots, the activity control is positioned at a first extent (e.g., 420 of FIG. 4) of the activity control. The activity control is in the first control region so the sound output power amplitudes or volumes and the sound frequency of playback for sounds that are included in the second and third groups of sounds are zero. The sound output power amplitude of sounds included in the first group of sounds increases as the position of the activity control moves from the left side of the plot to the right side of the plot. Likewise, the frequency of playback or repetition for sounds that are included in the first group of sounds increases as the activity control moves from the left side of the plot to the right side of the plot. The sound output power amplitude of sounds included in the first group of sounds ceases increasing when the activity control reaches the position of vertical line L1. Likewise, the frequency of playback or repetition for sounds that are included in the first group of sounds ceases increasing when the activity control reaches the position of vertical line L1.

Continuing to move from left to right in the plots, the sound output power amplitude and the frequency of playback for sounds included in the first group remain constant. The sound output power amplitude of sounds included in the second group of sounds increase as the position of the activity control moves from the position of vertical line L1 to vertical line L2. Likewise, the frequency of playback or repetition for sounds included in the second group of sounds increase as the activity control moves from the position of vertical line L1 to vertical line L2. The sound output power amplitude and the frequency of playback for sounds included in the third group remain zero. The sound output power amplitude of sounds included in the second group of sounds ceases increasing when the activity control reaches the position of vertical line L2. Likewise, the frequency of playback or repetition for sounds that are included in the second group of sounds ceases increasing when the activity control reaches the position of vertical line L2.

After the sound activity control reaches the position of line L2, the sound output power amplitude and the frequency of playback for sounds included in the first and second groups remain constant. The sound output power amplitude of sounds included in the third group of sounds increase as the position of the activity control moves from the position of vertical line L2 to the activity control extent (e.g., 424 of FIG. 4A) or end of travel. Likewise, the frequency of playback or repetition for sounds that are included in the third group of sounds increase as the activity control moves from the position of vertical line L2 to the activity control extent (e.g., 424 of FIG. 4A) or end of travel.

In this way, sounds from different sound groups may be blended together as an activity control changes position or state. Further, the frequency at which sounds are repeated may be increased or decreased as the position of the activity control is changed. Thus, a diversity of sounds may be generated via a single activity control to improve user experience.

Figure 6:
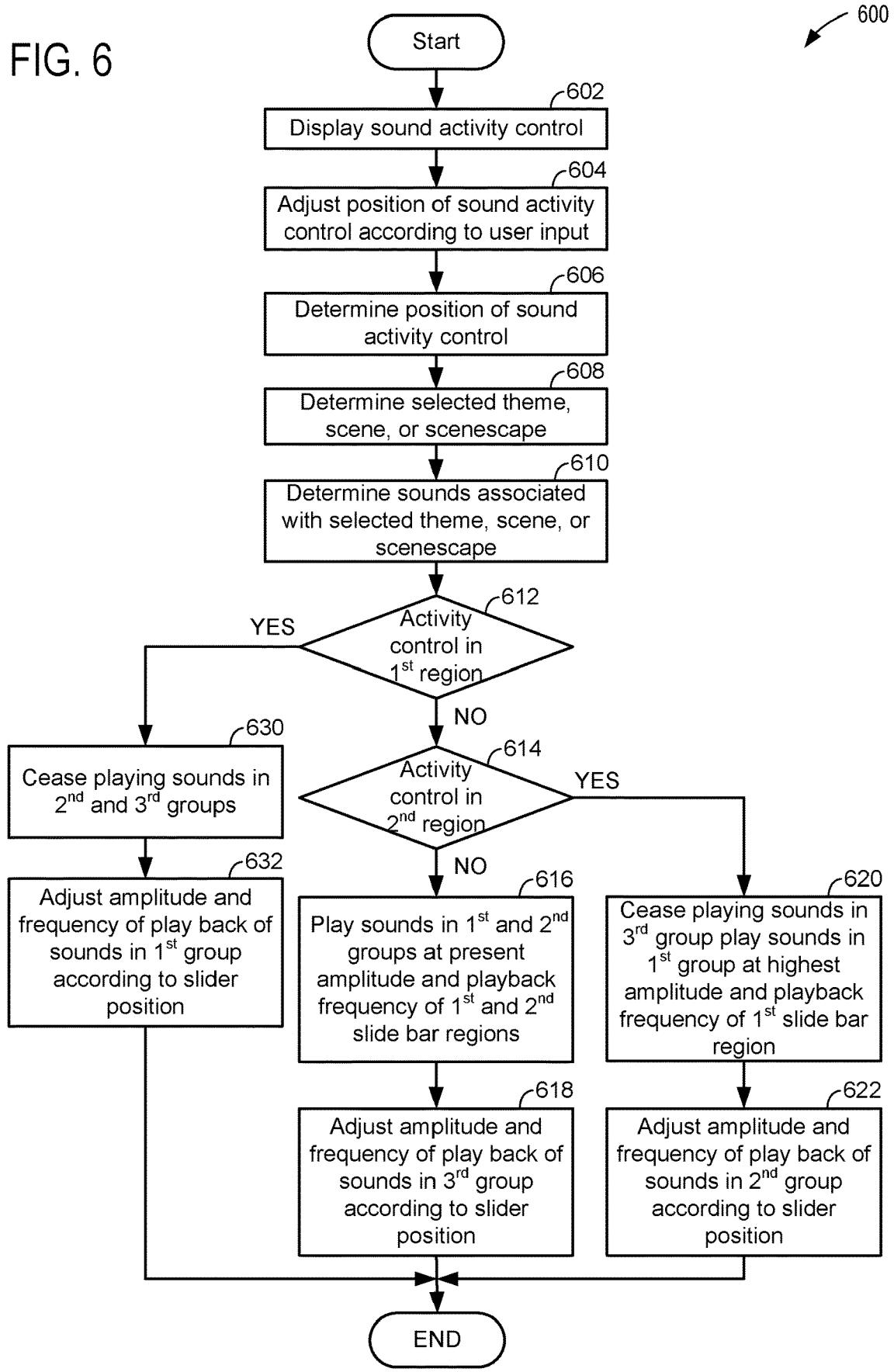
FIG. 6 shows a flow chart of an example method for generating sound via an audio or infotainment system.

FIG. 6 shows a flow chart for an example method 600 for adjusting audio output (e.g., in a vehicle). Method 600 may be performed by a computing system 109 and/or combination of computing systems and audio systems, which may include one or more computing systems integrated in a vehicle. For example, method 600 may be performed by executing instructions stored in memory of an in-vehicle computing system 109 alone or in combination with one or more other vehicle systems (e.g., audio controllers, CAN buses, engine controllers, etc.). The computing system 109 may perform method 600 including adjusting actuators (e.g., speakers) in the real world and perform operations internally that ultimately are a basis for adjusting actuators in the real world. One or more steps included in method 600 may optionally be performed.

At 602, the method 600 displays one or more activity controls (e.g., 400 shown in FIG. 4A) to a touch screen panel display. In one example, the one or more activity controls may take the form of a sound slider bar; however, in other examples, the activity control may take the form of a dial, knob, or other known user input device. Method 600 proceeds to 604.

At 604, method 600 receives data from a touch screen display to determine if a user is touching the display to indicate a desired state or position for the one or more sound activity controls. Method 600 determines if a user is attempting to adjust a position of the sound activity controls (e.g., slider bar 402 shown in FIG. 4A) and updates the position of the sound activity control if it is determined that the user is attempting to adjust the position of the sound activity control. Method 600 proceeds to 606.

At 606, method 600 determines the state or position of the sound activity control according to data received from the touch screen display or other user input device. Method 600 may also subdivide the control range of the sound activity control into a plurality of control regions as shown in FIG. 4B. For example, the control range of the sound activity control may be subdivided based on the actual total number of groups of sound elements (e.g., a first group of sound elements may be steady-state sound elements; a second group of sound elements may be dynamic sound elements; a third group of sound elements may be surreal sound elements) and physical dimensions of the sound activity control. Thus, if there are three sound element groups, the range of the sound activity control may be subdivided into three equal length control regions as shown in FIG. 4B. In other examples, the control regions may be a function of or based on surround sound control parameters or other sound control parameters. Method 600 may determine the state or position of the sound activity control and in which region of control the sound activity control is positioned according to data output via the touch panel display or other device. Method 600 proceeds to 608.

At 608, method 600 determines a theme, scene, or scenescape via receiving a selection from a user input device (e.g., a touch screen display). The theme, scene, or scenescape selections may include but are not limited to a desert, rain forest, sea shore, etc. In addition, in some examples, two or more themes, scenes, or scenescapes may be selected so that sounds from different themes, scenes, or scenescapes may be combined, if desired. Method 600 proceeds to 610.

At 610, method 600 determines sounds that are associated with the selected theme, scene, or scenescape. The sounds for the selected theme, scene, or scenescape may also be grouped. For example, a desert theme may include sounds of crickets included in a first group (e.g., steady-state) of sounds that also includes sounds of a light desert wind and/or sounds of a campfire. The desert theme may also include bird calls in a second group (e.g., dynamic) of sounds that also includes sounds of distant thunder. In addition, the desert theme may include coyote howling in a third group (e.g., surreal) of sounds that also includes sound of a distant train whistle. Thus, each theme, scene, or scenescape may be associated with one or more groups of sounds, and the one or more groups of sounds may be further differentiated by sound element classification (e.g., steady-state, dynamic, and surreal). The sounds may be retrieved from non-volatile memory when a theme, scene, or scenescape is selected. In addition, a visual representation of the selected theme, scene, or scenescape may be displayed via the in-vehicle computing system. Method 600 proceeds to 612.

At 612, method 600 judges if the sound activity control is positioned within a first control region according to output of a user input device. If method 600 judges that the sound activity control is within a first control region, the answer is yes and method 600 proceeds to 630. Otherwise, the answer is no and method 600 proceeds to 614.

At 614, method 600 judges if the sound activity control is positioned within a second control region according to output of a user input device. If method 600 judges that the sound activity control is within a second control region, the answer is yes and method 600 proceeds to 620. Otherwise, the answer is no and method 600 proceeds to 616.

It should be noted that although method 600 includes provisions for three control regions, the actual total number of control regions may be increased or decreased in a similar way. Additional sound element categories may be added by increasing the number of control regions.

At 630, method 600 ceases playing back or broadcasting sounds from the second and third groups of sound elements. Further, method 600 adjusts a sound output power of sounds that are included in the second and third groups of sound elements to zero. Method 600 also adjusts the frequency of playback or repetition of sounds that are included in the second and third groups of sound elements to a base rate (e.g., a slowest frequency that the sounds may be played back or broadcast via speakers). Thus, if the sound activity control is moved from a second control region to a first control region as may occur by moving slider bar 402 of FIG. 4B from right to left, sounds included in the second and third groups of sound elements are not played back or broadcast via speakers. Method 600 proceeds to 632.

At 632, method 600 plays (e.g., broadcasts via speakers) and adjusts volume or sound output power amplitudes and frequency of playback or repetition of sounds that are included in the first group of sound elements (e.g., steady-state sounds) associated with the selected theme, scene, or scenescape. The sound output power amplitude may be adjusted proportionately with a position of the activity control while the activity control is position within the first control region. For example, if the activity control is moved from left to right, the sound power amplitude or volume may increase proportionately with the adjustment of the activity control. Likewise, the frequency of playback or repetition of sounds that are included in the first group of sounds may be adjusted proportionately with the position of the activity control while the activity control is positioned within the first control region. For example, if the activity control is moved from left to right, repetition of a recording of sounds may increase proportionately with the adjustment of the activity control. One example of controlling sounds of a first group of sounds in this way is shown in the first and second plots from the top of FIG. 5 between the vertical axis and vertical line L1.

It should also be mentioned that the activity control may be configured to make other sound and/or sound system adjustments according to the control regions of the activity control beyond volume and frequency of repetition adjustments. For example, instead of adjusting the sound output power amplitude and frequency of repetition for sounds of a first group of sounds that are associated with the selected theme, scene, or scenescape, the sounds of the first group of sounds may be adjusted in other ways, including but not limited to adjusting the sounds according to surround sound up-mixer tuning parameters, delay time, reverberation, recreated or emulated sound venues (e.g., hall, stadium, theater, etc.), simulated distance to source of sound, and zonal sound control locations within a vehicle passenger cabin. As one example, adjusting the activity control position may move vehicle occupant's sound perception of listening to crickets chirp in the distance to listening right next to chirping crickets. In addition, where two or more activity controls are implemented or realized at once in the vehicle or by the in-vehicle computing system 109, one activity control may adjust sounds being played back, volume of sounds being played back, and frequency or repetition of sounds being played back. The other activity control may adjust surround sound up-mixer tuning parameters and zonal sound control within a vehicle. Method 600 proceeds to exit.

At 612, method 600 maintains playing sounds in the first group and in the second group at their present sound output power levels. Method 600 also maintains repetition rates of sounds in the first and second groups at their present frequency or rate. Thus, if the sound activity control is moved from a second control region to a third control region as may occur by moving slider bar 402 of FIG. 4B from right to left, sounds included in the first and second groups continue to be played back or broadcast via speakers as they were just before entering the third control region. Method 600 proceeds to 614.

At 614, method 600 adjusts volume or sound output power amplitudes and frequency of playback or repetition of sounds that are included in the third group of sound elements (e.g., surreal sounds) associated with the selected theme, scene, or scenescape. The sound output power amplitude may be adjusted proportionately with a position of the activity control while the activity control is position within the third control region. Likewise, the frequency of playback or repetition of sounds that are included in the third group of sounds may be adjusted proportionately with the position of the activity control while the activity control is positioned within the third control region.

One example of controlling sounds of a third group of sounds in this way is shown in the fifth and sixth plots from the top of FIG. 5 between vertical line L2 and the right limit of the plots. As previously mentioned, the activity control may be configured to make other sound and/or sound system adjustments according to the control regions of the activity control beyond volume and frequency of repetition adjustments. As one example, adjusting the activity control may move vehicle occupant's sound perception of listening to a coyote howling in the distance to listening right next to a howling coyote. In addition, where two or more activity controls are implemented or realized at once in the vehicle or by the in-vehicle computing system 109, one activity control may adjust sounds being played back, volume of sounds being played back, and frequency or repetition of sounds being played back. The other activity control may adjust surround sound up-mixer tuning parameters and zonal sound control within a vehicle. Method 600 proceeds to exit.

At 620, method 600 ceases playing back sounds that belong to the third group of sounds and maintains playing sounds in the first group and in the second group at their present sound output power levels. Method 600 also maintains repetition rates of sounds in the first group at their present frequency or rate. Thus, if the sound activity control is moved from a first control region to a second control region, or from a third control region to the second control region, sounds included in the first group of sounds continue to be played back or broadcast via speakers as they were just before entering the second control region. Method 600 proceeds to 622.

At 622, method 600 adjusts volume or sound output power amplitudes and frequency of playback or repetition of sounds that are included in the second group of sound elements (e.g., dynamic sounds) associated with the selected theme, scene, or scenescape. The sound output power amplitude may be adjusted proportionately with a position of the activity control while the activity control is position within the second control region. Likewise, the frequency of playback or repetition of sounds that are included in the second group of sounds may be adjusted proportionately with the position of the activity control while the activity control is positioned within the second control region. One example of controlling sounds of a second group of sounds in this way is shown in the third and four plots from the top of FIG. 5 between vertical line L1 and vertical line L2.

As previously mentioned, the activity control may be configured to make other sound and/or sound system adjustments according to the control regions of the activity control beyond volume and frequency of repetition adjustments. As one example, adjusting the activity control may move vehicle occupant's sound perception of listening to a bird calling in the distance to listening right next to a bird that is calling. In addition, where two or more activity controls are implemented or realized at once in the vehicle or by the in-vehicle computing system 109, one activity control may adjust sounds being played back, volume of sounds being played back, and frequency or repetition of sounds being played back. The other activity control may adjust surround sound up-mixer tuning parameters and zonal sound control within a vehicle. Method 600 proceeds to exit.

In this way, an activity control may be used to adjust sounds and sound controls for sounds that may be associated with a theme, scene, or scenescape. The activity control provides a simplified way of creating a personalized environment within a vehicle or other listening venue.

Thus, the method of FIG. 6 provides for a method for generating sounds in a vehicle, comprising: generating sounds according to a state of a user control that includes an operating range that is subdivided into a plurality of group regions, each of the plurality of group regions associated with one or more elements unique to a group region within the plurality of group regions. The method includes wherein generating sounds includes converting electrical signals into sounds via one or more speakers, wherein the plurality of regions are sound group regions, wherein the elements are sounds. The method includes wherein a first group of the plurality of sound group regions is a group steady-state sound elements. The method includes wherein a second group of the plurality of sound group regions is a group dynamic sound elements. The method includes wherein a third group of the plurality of sound group regions is a group surreal sound elements. The method further comprises increasing an actual total number of sounds generated according to the position of the user control in the plurality of group regions. The method further comprises increasing an actual total number of sounds generated according to the position of the user control in one of the plurality of group regions. The method includes wherein the one or more elements include surround sound control parameters, and further comprising: increasing a sound level according to the position of the user control in the plurality of group regions.

The method of FIG. 6 also includes a method for generating sounds in a vehicle, comprising: increasing a frequency of a sound generated and an audible sound level of the sound generated in response to a state of a single user control input device, the sound generated from a group of sounds stored in controller memory. The method includes where the sound generated is included in a first group of sounds corresponding to a first region of an operating range of a user control. The method further comprises adjusting a frequency of a second sound generated and an audible sound level of the second sound generated in response to the position of the single user control input device when the single user control input device is in a second region of the operating range of the user control, the second sound generated from the group of sounds stored in controller memory. The method further comprises increasing a frequency of a third sound generated and an audible sound level of the third sound generated in response to the position of the single user control input device when the single user control input device is in a third region of the operating range of the user control, the third sound generated from the group of sounds stored in controller memory. The method further comprises not adjusting the frequency of the second sound generated in response to the single user control input not being in the second region of the operating range. The method further comprises not adjusting the frequency of the third sound generated in response to the single user control input not being in the third region of the operating range.

Figure 7:
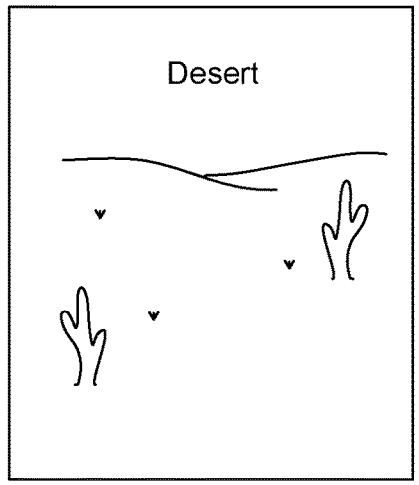
FIG. 7 shows example scene and sounds associated with the scenes.
Figure 7:
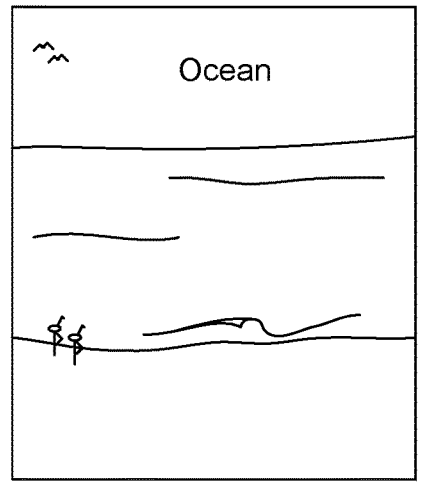

Referring now to FIG. 7, example scenes and their associated sound files are shown. FIG. 7 shows two example scenes and associated sound files that may be made available to a user to enhance a user's experience while traveling in a vehicle.

An example, desert scene 700 is shown. A user may wish to experience the sounds of a desert landscape. The user may select a desert scene and a picture or rendering of a desert may be shown on an in vehicle display screen as shown in FIG. 1 at 111. The desert scene may include a plurality of associated sound files 702-706 that are stored in controller non-volatile memory. The associated sound files may be grouped together according to the type of sounds or the way the sounds are applied via the in-vehicle computing system 109 or audio system 232. In this example, a first group of sounds 702 may be referred to as steady-state elements or sounds. The steady-state sounds in this example are sounds of crickets and sounds of a campfire. A second group of sounds 704 may be referred to as dynamic elements or sounds. The dynamic sounds in this example are sounds of owl hoots and sounds of bird calls. A third group of sounds may be referred to as surreal elements or sounds. The surreal sounds in this example are sounds of distant thunder and sounds of a coyote howling. Of course, the sound groups may be referred to in ways other than steady-state, dynamic, and surreal, if desired. The sound files may be played back or broadcast via speakers as described in the method of FIG. 6.

An example, ocean scene 750 is also shown. A user may wish to experience the sounds of an ocean front beach. The user may select an ocean scene and a picture or rendering of the ocean may be shown on an in vehicle display screen. The ocean scene may include a plurality of associated sound files 752-756 that are stored in controller non-volatile memory. The associated sound files may be grouped together as previously described. In this example, a first group of sounds 752 may be referred to as steady-state elements or sounds. The steady-state sounds in this example are sounds of waves and sounds of wind. A second group of sounds 754 may be referred to as dynamic elements or sounds. The dynamic sounds in this example are sounds of fish surfacing and birds calling. A third group of sounds may be referred to as surreal elements or sounds. The surreal sounds in this example are sounds of fog horns and ship horns. The sound files may be played back or broadcast via speakers as described in the method of FIG. 6.

The approach herein may utilize the above-described in-car tuning, mixing, and reproduction process to enable user-control of a variety of nature sounds. In one example, the process includes utilizing reference recording, such as with the three components described herein, sound design reproduction, and in-car up-mixing and dynamic routing. As noted, in one example, at least some of the reference recording data is obtained from the actual scene, where sound engineers travel to the location and capture spatially accurate audio/video field recordings, and capture the intended "emotional affect" of the scene. Additionally, local fauna, flora, and wildlife species must be noted for the later stages of the process.

For sound design reproduction—due to technical constraints of typical field recording equipment, the original field recordings may be reproduced from clean, representative audio samples. In some examples, the field recording might contain the sound of an owl hooting in the background, but these may also contain wind noise, ambient noise, and in general a high noise floor, rendering them less suitable for a critical listening environment like a premium branded audio vehicle. These sounds may then be reproduced from a sample library, gathered from cleaner close-mic recordings, or synthesized in some other manner.

Next, with regard to the in-car up-mixing and dynamic routing—the slider bars noted above herein may be used to enable the in-car mixing process. The reproduced samples may be injected into the vehicle signal path downstream of the surround sound upmixer (QLI) and upstream of the vehicle channel tuning parameters. This allows flexible, spatial control over the placement of these sounds. Typically may yield three types of sound elements as noted herein: steady-state base elements, dynamic elements, and surreal elements. These three types of elements can then me mixed in the vehicle to recreate a spatially accurate nature-scape that captures the spectral content of the space, as well as the spatial characteristics and the overall emotional affect as well.

In this way, it is possible to address the technical challenge of creating spatially accurate soundscapes in a vehicle of a wide variety with reduced storage and selection requirements. Likewise, it address the technical challenge of providing some tuning capabilities and flexibility, including a high level of flexibility in the spatial mixing process, which yields a more accurate NatureScapes experience in the car.

The description of embodiments has been presented for purposes of illustration and description. Suitable modifications and variations to the embodiments may be performed in light of the above description or may be acquired from practicing the methods. The methods may be performed by executing stored instructions with one or more logic devices (e.g., processors) in combination with one or more additional hardware elements, such as storage devices, memory, image sensors/lens systems, light sensors, hardware network interfaces/antennas, switches, actuators, clock circuits, etc. The described methods and associated actions may also be performed in various orders in addition to the order described in this application, in parallel, and/or simultaneously. Further, the described methods may be repeatedly performed. The described systems are exemplary in nature, and may include additional elements and/or omit elements. The subject matter of the present disclosure includes all novel and non-obvious combinations and sub-combinations of the various systems and configurations, and other features, functions, and/or properties disclosed.

As used in this application, an element or step recited in the singular and proceeded with the word "a" or "an" should be understood as not excluding plural of said elements or steps, unless such exclusion is stated. Furthermore, references to "one embodiment" or "one example" of the present disclosure are not intended to be interpreted as excluding the existence of additional embodiments that also incorporate the recited features. The terms "first," "second," and "third," etc. are used merely as labels, and are not intended to impose numerical requirements or a particular positional order on their objects. The following claims particularly point out subject matter from the above disclosure that is regarded as novel and non-obvious.

The invention claimed is:

1. A method for generating sounds in a vehicle, comprising:
generating sounds according to a longitudinal position of a position adjustable user input of a user control and an operating range of the user control that is subdivided into a plurality of group regions, at least one of the plurality of group regions associated with two or more sounds unique to a group region within the plurality of group regions, the position adjustable user input being moveable between the plurality of group regions; and
linearly increasing a frequency of a second sound and maintaining a frequency of a first sound in response to the position adjustable user input moving through one of the plurality of group regions.

2. The method of claim 1, wherein generating sounds includes converting electrical signals into sounds via one or more speakers, wherein the plurality of group regions are a plurality of sound group regions, wherein generating sounds includes increasing a sound output power of the first sound to a first level in response to a position of the position adjustable user input as the position adjustable user input is moved through a first group region of the plurality of group regions without increasing a sound output power of the second sound from zero and without increasing a sound output power of a third sound from zero, wherein generating sounds includes maintaining sound output power of the first sound at the first level and increasing the sound output power of the second sound to a second level as the position adjustable user input is moved through a second group region of the plurality of group regions without increasing the sound output power of sounds of the third sound from zero, and wherein the sound output power of the first sound remains at the first level and the sound output power of the second sound remains at the second level while the sound output power of the third sound increases as the position adjustable user input is moved through a third group region of the plurality of group regions.

3. The method of claim 2, wherein the first sound is a steady-state sound, and wherein the sound output power of the first sound increases linearly to the first level as the position adjustable user input moves linearly through the first group region.

4. The method of claim 3, wherein the second sound is a dynamic sound.

5. The method of claim 4, wherein the third sound is an unnatural sound.

6. The method of claim 1, further comprising increasing an actual total number of sounds generated according to a position of the position adjustable user input within the plurality of group regions.

7. The method of claim 1, further comprising increasing an actual total number of sounds generated according to a position of the position adjustable user input within one of the plurality of group regions.

8. A sound system of a vehicle, comprising:
one or more speakers; and
a controller electrically coupled to the one or more speakers including executable instructions stored in non-transitory memory that cause the controller to:
simultaneously increase a frequency of occurrence of a first sound to a first level and increase an audible level of the first sound to a second level, while maintaining a frequency of occurrence of a second sound at zero and maintaining an audible level of the second sound at zero in response to a longitudinal position of a user input; and
maintaining the frequency of occurrence of the first sound at the first level and maintaining the audible level of the first sound at the second level, while simultaneously increasing the frequency of occurrence of the second sound and increasing the audible level of the second sound in response to the longitudinal position of the user input, the first sound and the second sound generated via the one or more speakers according to the longitudinal position of the user input, the user input movable between a plurality of sound group regions of a user control.

9. The sound system of claim 8, wherein the user control includes an operating range that is subdivided into the plurality of sound group regions, each of the plurality of sound group regions including one or more sounds unique to a sound group region with the plurality of sound group regions, and wherein the one or more speakers are included within a vehicle passenger cabin.

10. The sound system of claim 9, further comprising additional executable instructions to generate sounds from only a first group of sounds included in a first sound group region of the plurality of sound group regions when the user input is positioned in the first sound group region.

11. The sound system of claim 10, further comprising additional executable instructions to generate sounds only from the first group of sounds and a second group of sounds included in a first sound group region and a second sound group region of the plurality of sound group regions when the user input is positioned in the second sound group region.

12. The sound system of claim 11, further comprising additional executable instructions to generate sounds from a first group of sounds, the second group of sounds, and a third group of sounds when the user input is positioned in a third sound group region.

13. The sound system of claim 12, further comprising additional executable instructions to change sound distribution from a first speaker to a second speaker and a third speaker according to a longitudinal position of a second user input in a first region of a second user control, and adjusting a level of up-mixed channels according to the longitudinal position of the second user input in a second region of the second user control.

14. A method for generating sounds in a vehicle, comprising:
simultaneously adjusting a frequency of a first sound generated and adjusting an audible sound level of the first sound generated in response to a longitudinal position of a single slide bar, and simultaneously adjusting a frequency of a second sound generated and adjusting an audible sound level of the second sound generated in response to the longitudinal position of the single slide bar, the first sound generated and the second sound generated from a group of sounds stored in controller memory, and wherein the first sound is different from the second sound.

15. The method of claim 14, wherein the audible sound level of the first sound generated is linearly increased when the single slide bar is in a first region, and wherein the audible sound level of the second sound generated is linearly increased when the single slide bar is in a second region.

16. The method of claim 15, wherein the first region is next to the second region, and wherein the audible sound level of the first sound generated is maintained at a non-zero level when the single slide bar is in the second region.

17. The method of claim 16, wherein the audible level of the second sound is zero in the first region.

18. The method of claim 17, further comprising not adjusting the frequency of the second sound generated when adjusting the frequency of the first sound generated.

19. The method of claim 14, further comprising changing sound distribution from a first speaker to a second speaker and a third speaker according to a position of a second adjustable user input in a first region of a second user control, and adjusting a level of up-mixed channels according to the position of the second adjustable user input in a second region of the second user control.

* * * * *